United States Patent
Saccardo et al.

(12) 
(10) Patent No.: US 6,471,649 B1
(45) Date of Patent: Oct. 29, 2002

(54) METHOD AND APPARATUS FOR STORING IMAGE INFORMATION IN AN ULTRASOUND DEVICE

(75) Inventors: Grace M Saccardo, Bolton, MA (US); Daniel Gerard Maier, Methuen, MA (US); Michael Hoar, Woburn, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 17 days.

(21) Appl. No.: 09/710,593

(22) Filed: Nov. 9, 2000

(51) Int. Cl.⁷ .................................................. A61B 8/00
(52) U.S. Cl. ........................ 600/437; 600/443; 348/65
(58) Field of Search ............................ 600/437, 443; 348/65, 232; 345/505; 710/313, 5

(56) References Cited

U.S. PATENT DOCUMENTS

| | | | |
|---|---|---|---|
| 5,295,485 A | * 3/1994 | Shinomura et al. | ......... 600/443 |
| 5,590,658 A | 1/1997 | Chiang et al. | |
| 5,603,323 A | 2/1997 | Pflugrath et al. | |
| 5,636,631 A | 6/1997 | Waitz et al. | |
| 5,690,114 A | 11/1997 | Chiang et al. | |
| 5,715,823 A | 2/1998 | Wood et al. | |
| 5,722,412 A | 3/1998 | Pflugrath et al. | |
| 5,817,024 A | 10/1998 | Ogle et al. | |
| 5,839,442 A | 11/1998 | Chiang et al. | |
| 5,851,186 A | 12/1998 | Wood et al. | |
| 5,879,303 A | 3/1999 | Averkiou et al. | |
| 5,891,035 A | 4/1999 | Wood et al. | |
| 5,893,363 A | 4/1999 | Little et al. | |
| 5,897,498 A | 4/1999 | Canfield et al. | |
| 5,938,607 A | 8/1999 | Jago et al. | |
| 5,957,846 A | 9/1999 | Chiang et al. | |
| 5,964,709 A | 10/1999 | Chiang et al. | |
| 5,997,479 A | 12/1999 | Savord et al. | |
| 6,007,490 A | 12/1999 | Pawluskiewicz | |
| 6,013,032 A | 1/2000 | Savord | |

(List continued on next page.)

OTHER PUBLICATIONS

Terason 2000 information obtained from url: www.terason.com/terason2000.htm; 6 pages.
Sonosite 180 information obtained from url: www.sonosite.com/products __180__heart.html; 5 pages.
SonoHeart Applications Summary obtained from the SonoSite brochure; 2 pages.

Primary Examiner—Marvin M. Lateef
Assistant Examiner—Ruby Jain
(74) Attorney, Agent, or Firm—John Vodopia

(57) ABSTRACT

In accordance with the present invention, a compact flash technology is utilized in an ultrasound device for storing digital images. The digital images preferably are stored in a standard format, such as, for example, the JPEG format, so that no specialized software is required to access and view the images. Compact flash technology is readily available to consumers and generally is relatively inexpensive. Also, relatively low cost interfaces are available for PCs and some printers to enable the digital images stored on a compact flash disk to be easily downloaded to a PC or printer. Additionally, standard PCs typically are equipped with software that can read JPEG files. Therefore, personal users of the ultrasound device can easily download images to their PCs and access and view the images without the need for special equipment, training, or personnel. When stored in such a standard format, no additional software is needed to view the images and thus the user can use his or her PC to access and view the images at no additional expense, provided the PC is equipped with hardware and/or software associated with the format. Although the images preferably are stored in the JPEG format on the compact flash disk, the images may be stored in other formats, such as, for example, the TIFF format, which is also a standard image format. Specialized software, such as DICOM or DSR, may also be utilized with the present invention if desired.

22 Claims, 5 Drawing Sheets

U.S. PATENT DOCUMENTS

| | | |
|---|---|---|
| 6,102,863 A | 8/2000 | Pflugrath et al. |
| 6,106,468 A | 8/2000 | Dowdell |
| 6,106,472 A | 8/2000 | Chiang et al. |
| 6,113,547 A | 9/2000 | Catallo et al. |
| 6,117,084 A | 9/2000 | Green et al. |
| 6,117,085 A | 9/2000 | Picatti et al. |
| 6,135,961 A | 10/2000 | Pflugrath et al. |
| 6,184,922 B1 * | 2/2001 | Saito et al. .................... 348/65 |
| 6,300,961 B1 * | 10/2001 | Finger et al. ................ 345/505 |
| 6,310,647 B1 * | 10/2001 | Parulski et al. ............. 348/232 |

* cited by examiner

METHOD AND APPARATUS FOR STORING IMAGE INFORMATION IN AN ULTRASOUND DEVICE

TECHNICAL FIELD OF THE INVENTION

The present invention relates to a method and apparatus for storing image information in an ultrasound device and, more particularly, to a method and apparatus for storing images in a standard format, such as JPEG (Joint Photographic Experts Group), for example, on a compact flash storage device in an ultrasound device so that the images can be easily archived, viewed, printed, etc., by the user.

BACKGROUND OF THE INVENTION

In the past, ultrasound systems have provided digital image storage in several ways. For example, it is known to provide digital image storage by networking images to a personal computer (PC) or server, or by storing images to a removable storage media, such as a magneto-optical disk. Although these solutions do offer digital storage and generally preserve image quality, they generally are not cost-effective or easy to use. Networks, servers and disk drives are expensive and often require specialized personnel to operate and administer. Additionally, the images are typically stored in a format specific to ultrasound technology, such as DSR (Digital Storage and Retrieval) or DICOM (Digital Imaging and Communications in Medicine), which are specifically designed for the medical community. Consequently, special software is required to view these images off-line. The special software is typically expensive and may require specialized personnel or training to operate.

Accordingly, a need exists for a method and apparatus for digitally storing ultrasound images in a format that can be easily archived, transferred to a PC, printed, viewed, e-mailed, etc., and which does not require specialized training or specialized hardware and/or software to utilize.

SUMMARY OF THE INVENTION

In accordance with the present invention, a compact flash technology is utilized in an ultrasound device for storing digital images. The digital images preferably are stored in a standard format, such as, for example, the JPEG format, so that no specialized software is required to access and view the images. Compact flash technology is readily available to consumers and generally is relatively inexpensive. Also, relatively low cost interfaces are available for PCs and some printers to enable the digital images stored on a compact flash disk to be easily downloaded to a PC or printer. Additionally, standard PCs typically are equipped with software that can read JPEG files. Therefore, personal users of the ultrasound device can easily download images to their PCs and access and view the images without the need for special equipment, training, or personnel.

When stored in such a standard format, no additional software is needed to view the images and thus the user can use his or her PC to access and view the images at no additional expense, provided the PC is equipped with hardware and/or software associated with the format. Although the images preferably are stored in the JPEG format on the compact flash disk, the images may be stored in other formats, such as, for example, BMP (bitmap), GIF (Graphics Interchange Format) (including animated GIF), or TIFF (Tagged Image File Format) formats, which is also a standard image format.

These and other features and advantages of the present invention will become apparent from the following description, drawings and claims.

DETAILED DESCRIPTION OF THE PREFERRED EMBODIMENT OF THE INVENTION

In accordance with the preferred embodiment of the present invention, ultrasound images captured by an ultrasound device are stored as still-frames on a compact flash card. The ultrasound device is equipped with an "image frame storage" control that causes the ultrasound system to enter a frozen imaging mode and then store the currently displayed image to the compact flash card in one of the aforementioned standard image formats. As stated above, preferably the images are stored in the JPEG format.

While the image data is being stored, preferably an "image frame storage in progress icon" appears on the display screen of the ultrasound device. The icon preferably displays the number of still-frame images that can be stored on the card after the current image is stored. When the storage operation is complete, the icon disappears. Also displayed on the screen, in accordance with the preferred embodiment, is an "image frame compression level" indicator that indicates the amount of compression that has been used to store the file.

The JPEG format is preferred due to its universal acceptance and the ubiquity of PC software to manage JPEG files. PCs and Internet browsers typically support reading JPEG files. Therefore, the customer or user is not required to purchase special software to enable images to be accessed and viewed. Images can also be stored in the DICOM format so that systems that are equipped with the special software required for this format can also access and view the stored images. The storage features and other features relating to the electrical control circuitry of the ultrasound device will be discussed in detail below with reference to FIG. 5.

Before discussing the electrical control circuitry of the present invention, an overall discussion of an ultrasound device with which the electrical control circuitry of the present invention preferably is used will be provided. However, it should be noted that the electrical control circuitry of the present invention is not limited with respect to the type of ultrasound device with which it is implemented. In accordance with the preferred embodiment, the electrical control circuitry of the present invention is incorporated into a small, hand-carriable ultrasound device that is especially suitable for use by laypersons without extensive formal sonographic training.

Figure 1:
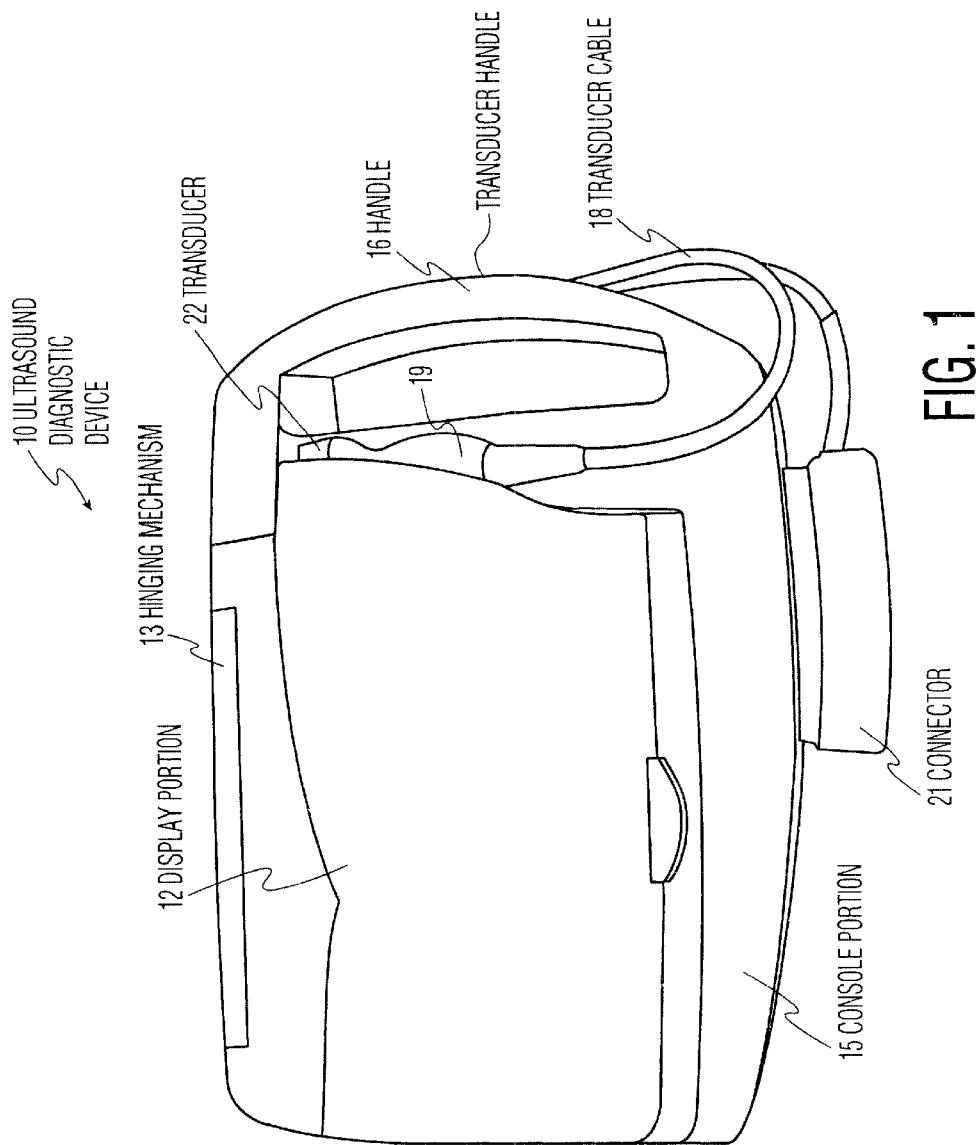
FIG. 1 is a top perspective view of the ultrasound diagnostic device of the present invention in accordance with the preferred embodiment.

FIG. 1 is a pictorial representation of the ultrasound diagnostic device 10 of the present invention in accordance with the preferred embodiment. The ultrasound diagnostic device 10 is approximately 10½ inches long, approximately 8 inches wide and approximately 2¾ inches thick, although those skilled in the art will understand that it is not limited to these exact dimensions. The weight of the device 10 is less than 7 pounds, including the electrical control circuitry, the battery pack, and the transducer assembly. The manner in which this light-weight design has been achieved is attributable to the overall design and construction of the device 10 and to the selection and configuration of the electrical and data storage components implemented in the device 10.

The device 10 is similar in design to a laptop computer. The device 10 comprises a console portion 15 and a display portion 12. To open the device 10, the user opens the display portion 12 by unlatching and lifting up on the tab 14 located on the display portion 12. The display portion 12 is coupled by a hinging mechanism 13 to the console portion 15 so that when the user lifts up on the display portion 12, it rotates upwards (i.e., away from the console portion 15). The hinging mechanism 13 preferably is similar to hinging mechanisms typically used with laptop computers currently available on the market. A handle 16 is integrally connected to the console portion 15 to allow the device 10 to be easily carried by hand.

A transducer assembly is removably connected by a connector 21 to the ultrasound diagnostic device 10 and comprises a transducer cable 18, a transducer handle 19, and a transducer 22. The connector 21 comprises a latch (not shown) which engages a mating mechanism (not shown) comprised in the console portion 15. Preferably, the transducer handle 19 is small enough to fit comfortably in the palm of the hand of the user so that it can be easily manipulated by the user.

The connector 21 enables different types of transducer assemblies to be implemented with the ultrasound diagnostic device 10. Depending on the bodily feature being imaged, different transducer assemblies can be utilized with the ultrasound diagnostic device 10. The user can easily unplug one type of transducer assembly and easily plug another transducer assembly into the receptacle of connector 21. Of course, each transducer assembly must be adapted to mate with the connector 21. This provides the ultrasound diagnostic device 10 with great flexibility with respect to its applications, as will be understood by those skilled in the art. For example, rather than using a stethoscope to check a patient's heart beats, the user may connect the appropriate transducer assembly to the device 10 and use the device 10 in the same manner in which a conventional stethoscope is used. In contrast, the ultrasound diagnostic device may be used by a gynecologist to perform fetal monitoring. In this case, a transducer assembly which is suitable for this purpose will be plugged into the receptacle.

When the ultrasound diagnostic device 10 is intended to be used with transducer assemblies that are implemented for different imaging purposes, the ultrasound diagnostic device 10 will be equipped with software and/or hardware that is capable of acquiring and processing the various types of imaging information, as will be understood by those skilled in the art. The ultrasound diagnostic device 10 may be switched between imaging modes which correspond to different transducer assemblies. In this case, the ultrasound diagnostic device 10 may comprise different software driver modules for each of the different transducer assemblies.

The ultrasound diagnostic device 10 comprises a central processing unit (FIG. 5), e.g., a microprocessor, which controls the operations of the ultrasound diagnostic device 10. When the user switches from one mode to another, the central processing unit (CPU) simply executes the appropriate software module to enable the CPU to acquire and process the image data obtained by the transducer assembly, as will be understood by those skilled in the art. The software modules may be stored in a system memory device, which is in communication with the CPU, as discussed below in detail with reference to FIG. 5.

Figure 2:
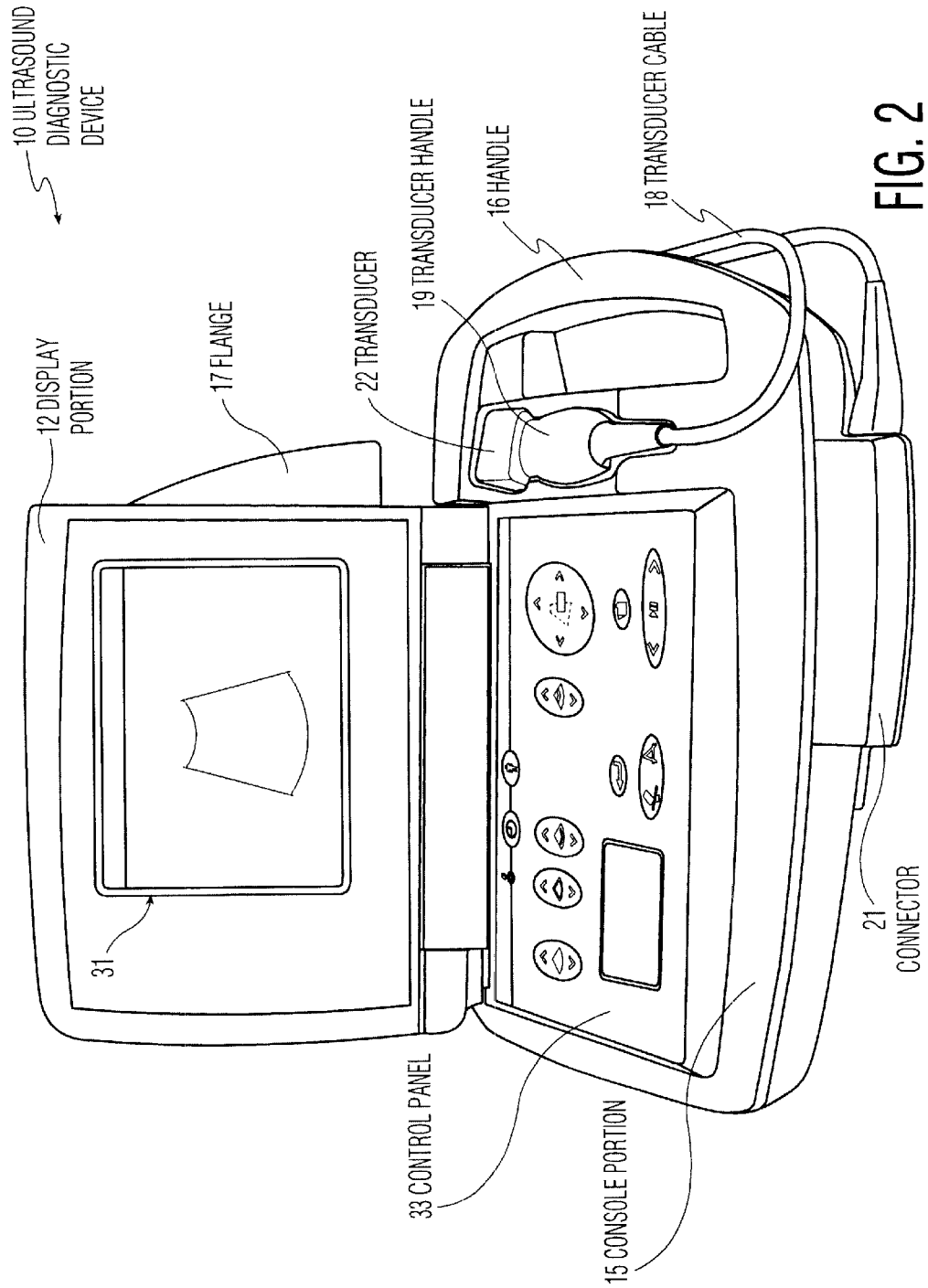
FIG. 2 is a front perspective view of the ultrasound diagnostic device shown in FIG. 1 with the display screen placed in a viewing position.

FIG. 2 illustrates the ultrasound diagnostic device 10 with the display portion 12 placed in a viewing position. Preferably, the display portion 12 contains a display screen 31, comprising for example a liquid crystal display (LCD) screen. The console portion 15 comprises a small control panel 33 having various input keys, which preferably have icons on them. By using icons on the keys, a single control panel 15 can be used in different countries around the world because the icons preferably are selected so that their meanings are well known to those who perform ultrasound diagnostic imaging tasks, as will be understood by those skilled in the art.

Preferably, the display portion 12 and the console portion 15 are comprised of cast metal and molded plastic to provide the ultrasound diagnostic device 10 with a rugged encasement. The ultrasound diagnostic device 10 is designed to withstand external impact resulting from, for example, dropping the device 10 or collisions between the device 10 and external objects. Furthermore, the ultrasound diagnostic device 10 folds, as described above, such that when it is not in use, the display screen 31 and the control panel 33 are protected from external forces. The transducer connector 21 is also designed of the same or similar types of materials so that it can also withstand shocks from external forces. A flange 17 helps hold the transducer portions 19 and 22 in place when the device 10 is not in use and protects these portions of the transducer assembly.

Figure 3:
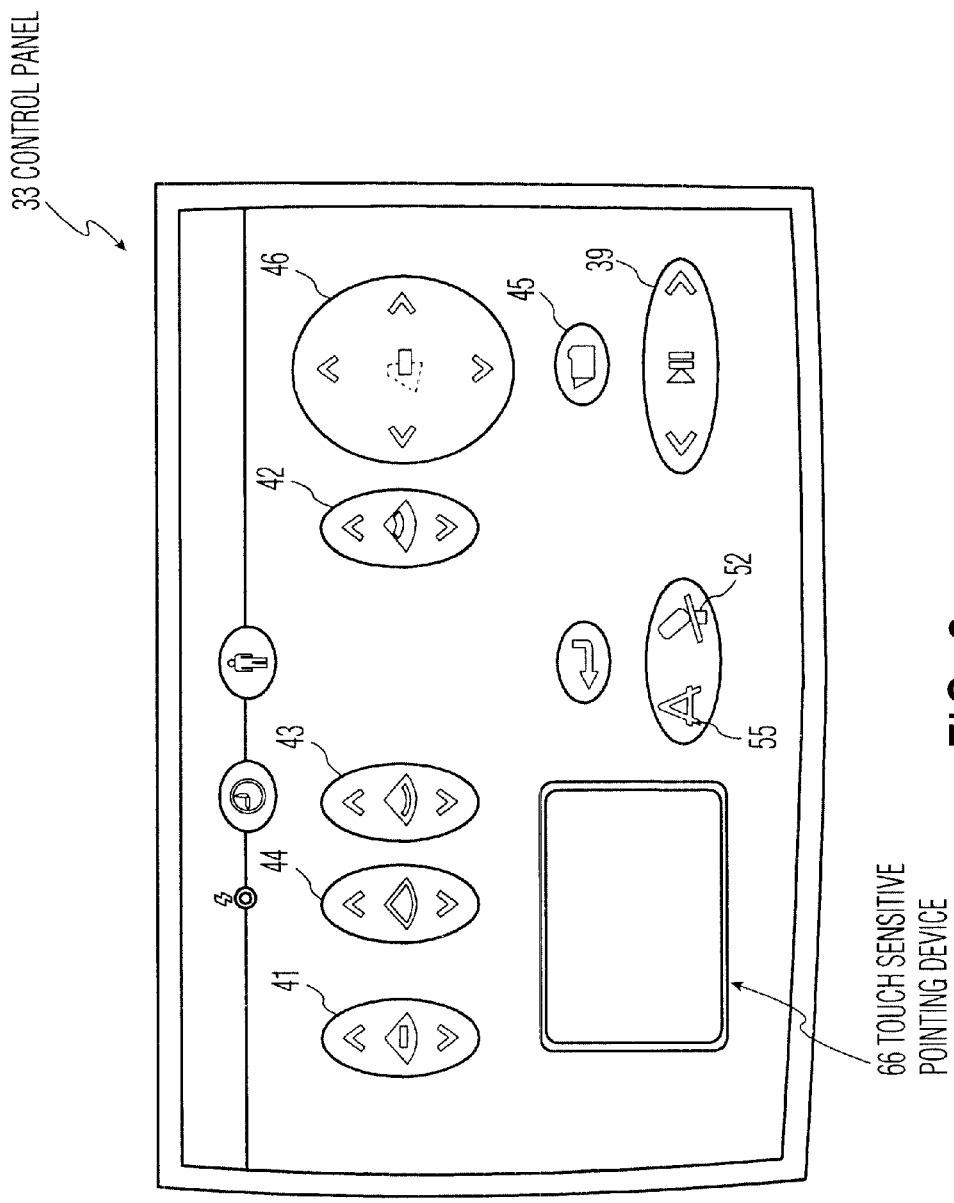
FIG. 3 is a top view of the control panel of the ultrasound diagnostic device of FIG. 1, which illustrates the icons located on the input keys.

FIG. 3 is a top view of the control panel 33 of the ultrasound diagnostic device 10. In accordance with the preferred embodiment of the present invention, all system controls are "one button-one function", i.e., each key corresponds to a command which tells the central processor to perform a particular function. The keys preferably are logically and ergonomically grouped in such a manner that they can be easily identified and so that their meanings are self-explanatory. It should be noted that the control panel 33 is not limited to the particular buttons and icons shown in FIG. 3. The particular buttons and icons shown in FIG. 3 are discussed herein for the purposes of demonstrating the preferred "one key per function" features of the present invention. Also, it is not necessary that buttons be used on the control panel 33. Any kind of actuation device(s) can be used on the control panel 33 to allow a user to input data and/or commands on the control panel 33.

Preferably, all of the buttons are membrane keys. The stop button 39 is actuated by the user in order to freeze an image being displayed on the display monitor. For example, if an image is being displayed on the display monitor at a rate of 30 frames per second, activating the stop button 39 will freeze the last image that was being displayed when the button 39 was activated. The electrical control circuitry will cause this image to continue to be displayed either for a predetermined period of time or until the button on the console is reactivated. In the exemplary embodiment, when the button 39 is activated a second time (i.e., toggled), the device 10 will resume displaying the images in real time as they are acquired. The shape of the freeze button 39 preferably is a universal symbol, which facilitates ease of use of the ultrasound diagnostic device by the user.

The pie-slice-shaped icon 41, which has "cm" in the center of it and arrow heads above and below it, represents the image sector, which is commonly referred to as a B-mode image sector, seen by the user on the display monitor. The button 41 is used to adjust the depth of the image being displayed. For example, if the depth of the image being displayed is 8 centimeters and the user desires to view an image at a depth of from 0 to 4 centimeters in the body, the user depresses the button 41 at the location of the up arrow. The display monitor will display information corresponding to the depth of the image being displayed.

The three buttons 42, 43 and 44 are gain variance control buttons. The user uses these buttons to control what is commonly referred to as time gain compensation (TGC). The electrical control circuitry preferably comprises a time gain amplifier (not shown) which varies gain with respect to time. As acoustical energy is propagated into the body by the transducer, the body absorbs some of the energy, while some of the energy is reflected back out of the body and received by the transducer. The strength of this echo will vary depending on the distance that the object that caused the echo is away from the transducer. Therefore, in many cases it is desirable or necessary to amplify the echoes. The button 44 is used to control the overall gain of the image being displayed. To decrease the gain, the user depresses the button 44 at a location on the down arrow. To increase the gain, the user depresses the button 44 at a location on the up arrow.

The button 43 is used to increase and decrease the gain of echoes that correspond to targets in the top section of the displayed image. This section of the displayed image corresponds to targets that are relatively close to the transducer. The button 42 is used to increase and decrease the gain of color flow. Button 45 has an icon on it that represents a folder. This can be used to store, for example, an image frame that has been frozen by activating the freeze button 39. The button 46 is utilized to position a superimposed Color Flow Doppler image over the B-Mode image being displayed on the display monitor. In ultrasound imaging, colors are utilized to represent velocity. The well-known Doppler effect is utilized to determine the velocity of the target being imaged and to encode the image data with colors. For example, if blood is flowing towards the transducer, the blood is typically represented in yellow or red on the display monitor, depending on the velocity of the blood. If blood is flowing away from the transducer, it is typically displayed in blue on the display monitor. For example, if the user is viewing a vessel in which all the blood is flowing away from the transducer, the vessel would be colored blue. If the user is viewing a vessel in which all of the blood is moving towards the transducer, the vessel would be colored yellow or red, depending upon the velocity.

The button 46 allows an image sub-sector that is colored to be superimposed over the B-mode image sector being displayed. The B-mode image may be, for example, a sector image that is 90 degrees in width. The button 46 allows the user to shift the superimposed color sector to any location over the B-mode image sector by using the arrow keys. The button 48 is used to turn the color flow on and off and to select the type of color flow to be displayed.

The functions of the buttons 52, 55 and 58 will be described with respect to an imaging example in which the ultrasound diagnostic device 10 is used to obtain an image of a baby's head. As the transducer is being used to acquire the image, if the freeze button 39 is depressed, the image on the display monitor will be frozen. The button 55 having the icon of a pair of calipers thereon may then be depressed, which causes a cross mark similar to a cursor to be displayed on the display monitor. The distance between the cross mark location and the transducer (the depth of the cross mark) is displayed. The user may then move the cross mark around with his or her fingertip by using the touch-sensitive pointing device 66. When the cross mark has been placed by the user over the point of interest in the image, the user depresses the caliper button 55 again. This causes the first cross mark to be anchored and a second cross mark to be displayed on the display monitor. The user then moves the second cross mark until it has been placed over another point of interest on the image. As the second cross mark is moved, the distance between the two cross marks will be displayed on the display monitor in centimeters and fractions thereof.

Selecting the Image Frame Storage Control mode (button 45) causes the ultrasound device to enter Frozen Imaging mode (if it isn't already frozen), and then store the currently displayed image to the compact flash card in JPEG format (or other standard format). While the storage is in progress, an "Image frame storage in progress" icon (not shown) appears on the display screen. This icon displays the number of still frame images that can be stored on this card after this image. When the storage operation is complete, the icon is removed. Also displayed on the display screen is an "Image frame compression level" (not shown). This is an indicator of how much, if any, compression was used when storing the file.

Each time the caliper button 55 is depressed, another cross mark will be displayed up to a maximum of four cross marks. This enables the user to measure up to two distances between objects in the body being displayed. If the user does not like where one of the cross marks is anchored, the user can depress the erase button 52, which will cause the most recent cross mark to be erased. Button 58 is used to allow the user to enter identification information about the patient.

Figure 4:
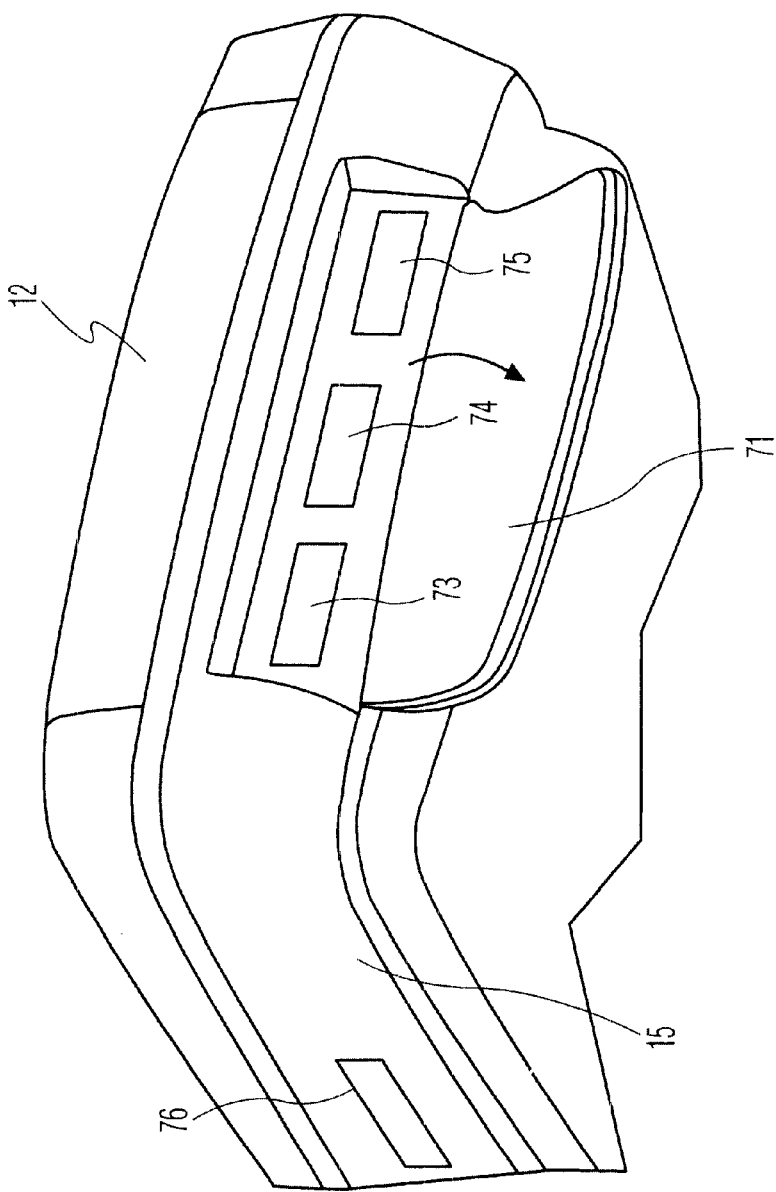
FIG. 4 is a rear perspective view of the ultrasound diagnostic device shown in FIG. 1.

FIG. 4 is a rear, perspective view of the ultrasound diagnostic device 10. This view shows a rear cover panel 71, which can be opened and closed to allow various data storage and transmission devices to be connected to the ultrasound diagnostic device 10 via ports 73, 74 and 75. For example, one of the ports 73 may be used as a network connection to enable data to be loaded into and downloaded from the ultrasound diagnostic device 10. One of the ports 74 may be used for an infrared receiver and transmitter diode pair, which can be used to establish an optical data path between the ultrasound device, and (not shown) another computer, printer, network connection, or mass storage device. Another port 75 may be used as an alternate, non-optical means to allow, for example, a computer or printer (not shown) to be connected to the ultrasound diagnostic device 10 to enable data to be loaded into and downloaded from the ultrasound diagnostic device 10.

Port 76, which preferably is located on the side of the console portion 15, is adapted to receive a compact flash card, which functions as a mass storage device. Use of the compact flash card enables large quantities of imaging data to be downloaded from the ultrasound device 10. One of the advantages of using a compact flash card as a mass storage device is, in addition to the capability of storing large amounts of data, they are very small in size, typically on the order of one or two square inches.

Figure 5:
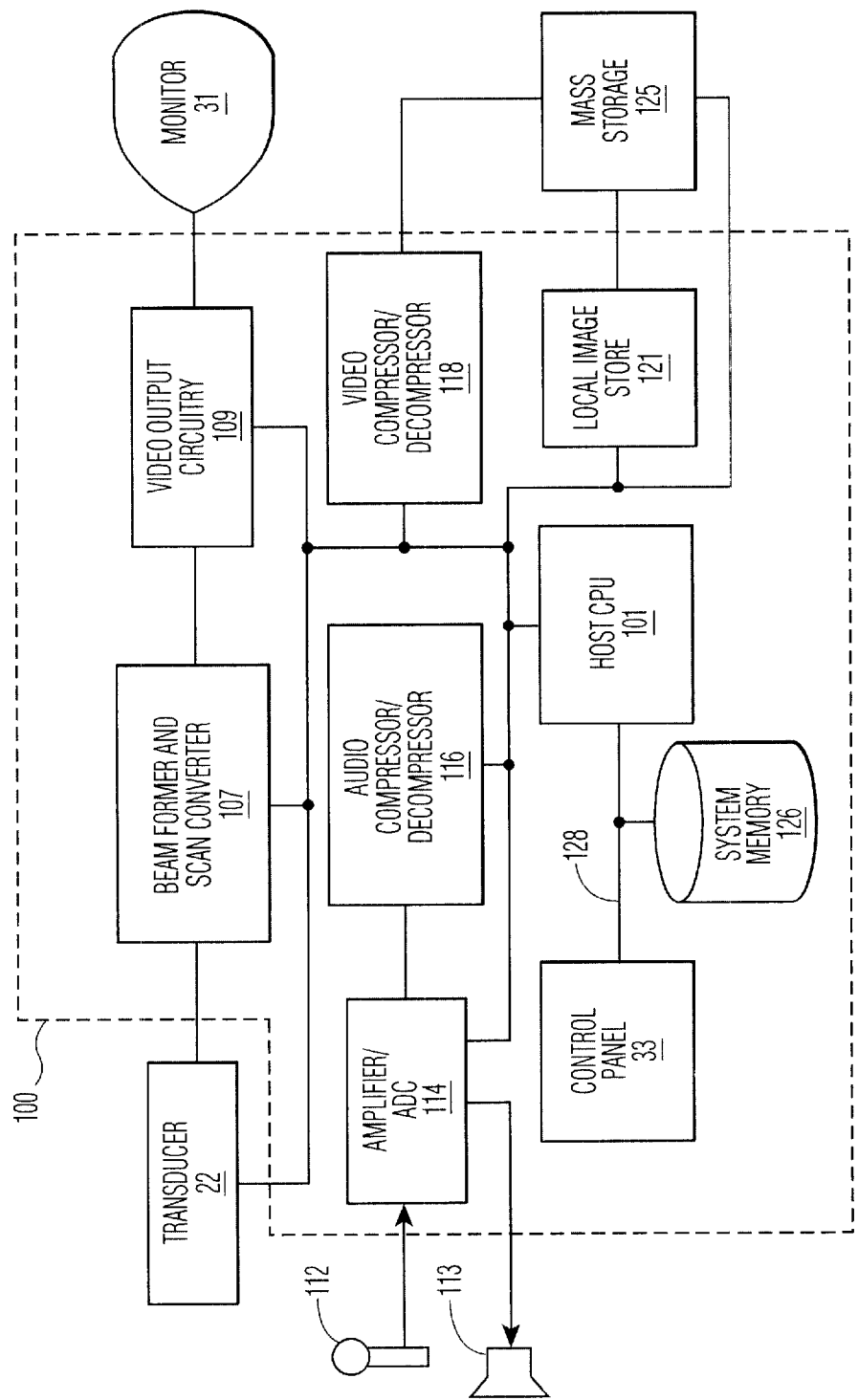
FIG. 5 is a block diagram of the electrical control circuitry and software of the ultrasound diagnostic device of the preferred embodiment.

FIG. 5 is a block diagram of the electrical control circuitry 100 of the present invention in accordance with the preferred embodiment. The electrical control circuitry 100 is electrically coupled to the transducer 22, to the display monitor 31 and to a mass storage device 125. Preferably, the electrical control circuitry 100 is also electrically coupled to an audio input device 112 (e.g, a microphone) and to an audio output device 113 (e.g., a speaker).

The ultrasound image acquisition component is comprised of a beam former/scan converter 107 and a transducer 22. The beam former/scan converter component 107 generates electrical signals necessary to cause transducer 22 to form an acoustic beam by launching a shaped acoustic wave. Reshaped acoustic waves which are returned from discontinuities in the body are returned to the transducer, and reconverted into electrical signals. These signals are processed by the beam former/scan converter component 107 and stored in the appropriate pixels in the appropriate frame of local image storage device 121. As the acoustic beam is steered in different directions by the beam former/scan converter component 107, and the transmission/reception process is repeated by beam former/scan converter component 107, different pixels in the selected frame of local image storage device 121 are filled in with image data.

When all of the specified acoustic lines have been shot, a cross-sectional map of the property of the body being examined, such as, for example, tissue velocity, or acoustic impedance, the corresponding digital image data will have been placed in the specified frame of local image storage device 121. The necessary sub-functions performed by a beam former/scan converter component 107 are well known to those skilled in the art, and are documented in many publicly available books and articles. A readily available example of such a description may be found in Chapters 3, 4 and 6 of a book entitled *Diagnostic Ultrasound Principles, Instruments, and Exercises,* Third Edition, by Frederick W. Kremkau, PhD., W B Saunders Company, 1989, which is incorporated herein by reference.

Each page of the local image storage device 121 contains the data for one frame that is to be displayed on the display monitor 31. This memory device, which preferably is a fast semiconductor memory device, may contain many frames or as few as two frames, but typically less than 100 frames, due to the cost of this type of memory device. An example of a semiconductor memory device that is suitable for implementation as the local image storage device 121 is a Synchronous DRAM (dynamic random access memory) integrated circuit chip, such as, for example, an NEC 4516161-10 DRAM integrated circuit chip, manufactured by NEC Corporation. This particular memory device is capable of storing 4 megabytes of 16 bit words. Preferably, the local image storage device 121 is comprised of a plurality of these integrated circuit chips. However, those skilled in the art will understand that the present invention is not limited with respect to the amount of memory comprised by the local image storage device 121 or with respect to the type of memory device utilized for this purpose.

The video output circuitry 109 formats the data in accordance with a predetermined horizontal and vertical synchronization technique appropriate for the display monitor 31. The video output circuitry 109 also translates the data into either color data or black-and-white data, depending upon the data stored in local image storage device 121, and the requirements of the display monitor 31. Graphics and text may be generated by the host CPU 101 and added to the image frames by the video output circuitry 109.

The host CPU 101 executes programs stored in system memory 126 and receives commands from the control panel 33 in response to commands entered by a user (not shown) on the control panel 33. The CPU 101 processes these commands in a manner dictated by one or more programs being executed by the CPU 101. Many of these commands correspond to operations to be performed on the ultrasound image, as discussed above with reference to FIG. 3. The host CPU 101 translates these commands into control data to be output to the video output circuitry 109 and/or to the beam former/scan converter component 107. The operations of the beam former/scan converter component 107 and of the video output circuitry 109 are controlled via these commands.

The beam former/scan converter component 107, the local image storage device 121, and the video output circuitry 109 operate in conjunction with one another in response to the commands received from the CPU 101 to perform operations on the ultrasound image. The manner in which these components cooperate with one another to perform these operations is well known to those skilled in the art. Therefore, in the interest of brevity, a detailed discussion of the operations of these components will not be provided herein.

Several video output circuitry components are available on the market that are suitable for performing the formatting and translation functions of the video output circuitry 109. Similarly, a plurality of transducers are available on the market that are suitable for performing the functions of the transducer 22. Preferably, the transducer 22 is a 2.5 megahertz phased array sector transducer sold by Agilent Technologies, Inc. Often times, it is desirable to store many seconds of the ultrasound image. For example, it may be desirable to capture many segments of heart activity. As stated above, the local image storage device 121 typically is too small for this purpose. The local image storage device 121, due to the high cost of fast, semiconductor memory, generally holds anywhere from two to one hundred pages of image data. This problem is solved by utilizing an additional mass storage device 125, which preferably utilizes Compact Flash technology, as discussed below in more detail.

To further reduce the cost of mass storage per stored page, image data from local image storage device 121 preferably is routed through video compressor/decompressor 118. As image data is routed from image memory 121 to mass storage device 125, it is compressed. As data is routed from mass storage device 125 to local image storage device 121, it is decompressed. Compression ratios of ten or fifteen to 1 are achievable with little or no degradation of the image. However, the present invention is not limited to any particular compression ratios.

The images that are stored on the compact flash card 125 preferably are stored in JPEG format. By utilizing compact flash technology and storing images in the JPEG format, the images can be easily archived, transferred to a PC, printed, viewed, emailed, incorporated into presentations, etc. Suitable compact flash technology for use with the present invention is produced by SanDisk Corporation. This technology is readily available to consumers and is relatively inexpensive. Low cost compact flash interfaces are available for PCs, and some printers have built-in compact flash interfaces. Additionally, this technology is easy for consumers to use and requires no specialized personnel or training to operate.

Additionally, by storing images in JPEG format, no specialized software is required to access and view the images. Standard desktop PCs typically come with software that can read JPEG files, so users can easily access their images without special equipment, training, or personnel and at no additional expense. Of course, those skilled in the art will understand that images can be stored in other standard formats, such as the BMP, GIF or TIFF formats, for example. Preferably, the Video Compressor/Decompressor component 118 that provides the compression/decompression functions in accordance with the JPEG or other standard imaging format is implemented in software that is executed by the CPU 101. However, these functions could also be performed in hardware or a combination of hardware and software, as will be understood by those skilled in the art.

The JPEG format provides video compression and decompression to be performed using standard JPEG algorithms. A wavelet compression algorithm is another example of a compression algorithm that may also be used for this purpose. JPEG compression and decompression algorithms can be performed in hardware using a particular integrated circuit or in software being executed on the CPU 101, which preferably is a microprocessor. Wavelet compression algorithms can also be performed in hardware and/or software. A suitable video integrated circuit chip for performing video compression and decompression is produced by Zoray Corporation and is marketed as model number ZR36050. This particular video integrated circuit chip utilizes the JPEG compression standard. With respect to audio compression and decompression, several standard compression/decompression algorithms are available on the market. For example, a computer program known as Microsoft ADPCM Codec, which is commonly supplied with Windows 95 or 98 by Microsoft Corporation of the State of Washington, is suitable for performing audio compression/decompression.

The compact flash technology utilized enables files to also be stored in DICOM format. Software executed by the CPU 101 works in conjunction with the compact flash card to enable images to be stored thereon in this format. Therefore, systems that are equipped with the special software required for this format can also access and view the stored images downloaded from the ultrasound device 10 to the compact flash disk 125. Therefore, although the ultrasound diagnostic device 10 preferably is designed for use by a layperson, it is not limited to this use. It is also suitable for use in healthcare facilities by persons with specialized training, as will be understood by those skilled in the art. Further, as the images can be stored in a non-medical standard format, such images can be transmitted to the patient for viewing on a standard home PC.

The ultrasound diagnostic device 10 comprises a network connection to enable the electrical control circuitry 100 to be interfaced with a network. This type of connection allows the image information stored in the local image store 121 and/or in the mass storage device 125 to be downloaded directly onto a network. As stated above with reference to FIG. 4, the ultrasound diagnostic device 10 preferably comprises a port 73 that functions as a network connection to allow the user to insert, for example, an Ethernet card (not shown) into the network connection port 73 of the ultrasound diagnostic device 10 to allow the image data to be downloaded directly onto a network. An optical link, such as, for example, an Infrared link (port 74), may also be used to allow data to be downloaded from and loaded into the ultrasound diagnostic device 10.

In accordance with the preferred embodiment of the present invention, the electrical control circuitry 100 allows the user to generate audio files, which are appended to the ultrasound images to which they correspond. To accomplish this goal, the control panel portion 15 of the ultrasound diagnostic device 10 has an audio input port (not shown) adapted to allow an audio input device 112, such as a microphone, to be coupled to the electrical control circuitry 100. An amplifier and analog-to-digital converter component 114 receives analog signals from the audio input device 112 and performs amplification and analog-to-digital conversion to obtain a digital audio image. The host CPU 101 may then cause the digital audio image information to be compressed by audio compressor/decompressor component 116 and stored in a memory device, such as mass storage device 125.

The host CPU 101 also determines which audio information corresponds to the associated image information. The host CPU 101 can perform this function in a plurality of manners, as will be understood by those skilled in the art. For example, the host CPU 101 can be programmed to tag the audio files with tags that associate the audio files with their respective image files. When the audio files and the image files are stored in the mass storage device 125, the tags that associate the audio files with the image files are also stored in the mass storage device 125. The audio files can be associated with the image files by using other techniques, such as, for example, storing audio files and image files in such a manner and in accordance with a predetermined ordering convention that the host CPU 101 can easily determine which files are audio files, which files are image files, and which image files are associated with which audio files. By way of example, images and sound can be stored in the MPEG format. Those skilled in the art will understand how these tasks can be accomplished.

Under control of the host CPU 101, audio files may be read out of the mass storage device 125, decompressed, if necessary, in audio compressor/decompressor 116, and played back over audio output device 113. Also, the mass storage device 125 having the audio files and the image files stored therein may be removed from the ultrasound diagnostic device 10 and placed in an external read/write device (not shown) to allow the image information and the audio information to be downloaded from the mass storage device 125 to an external computer or memory device. As will be understood by those skilled in the art, the external computer will be configured with compact flash technology to allow the image files and audio files to be read off of the mass storage device 125, decompressed, if necessary, and presented to the user via appropriate output devices.

It should be noted that the audio compressor/decompressor component 116 may also be implemented in hardware, software executed by the CPU 101, or in a combination of hardware and software. Several audio and video compressors and decompressors are available on the market that are implemented entirely in hardware or entirely in software, or in a combination of hardware and software. An audio compression/decompression integrated circuit chip which is suitable for performing audio compression and decompression is manufactured by Cirrus Logic and is sold as model number CS4215.

The present invention has been described with reference to the preferred embodiments, but is not limited to these embodiments. Those skilled in the art will understand that various modifications can be made to the embodiments described herein that are within the scope of the present invention. For example, although one important feature of the present invention is that the ultrasound device has been uniquely designed for use by laypersons so that it can be easily used by users and patients (i.e., persons other than sonographers), use by such persons is within the scope of the invention. Another example relates to the image data formats with which the present invention may be implemented. Although a few standard image data formats have been explicitly mentioned herein, other image data formats that are currently in use or that become available in the future may also be suitable for use with the present invention.

What is claimed is:

1. An ultrasound diagnostic device comprising:

an ultrasound image acquisition component;

a processor in communication with the ultrasound image acquisition component; and a port in communication with the processor, the port being designed to receive a compact flash card, wherein ultrasound image data acquired by the image acquisition component is processed in accordance with a particular image format such that the processed image data is suitable for storage on a compact flash memory device.

2. The device of claim 1, further comprising:

a compact flash memory device, the compact flash memory device being removably coupled to said port to enable the processed image data to be stored on the compact flash memory device.

3. The device of claim 1, further comprising:

a compact flash memory device coupled to said port, wherein the processor is configured to execute a compression algorithm and a decompression algorithm, the compression and decompression algorithms being compatible with said particular image format, wherein when the processor executes the compression algorithm, the ultrasound image data acquired by the image acquisition component is compressed in accordance with said particular image format and stored on said compact flash card, and wherein when the processor executes the decompression algorithm, the processor causes compressed image data stored on the compact flash memory device to be read from the compact flash memory device and decompressed in accordance with the particular image format.

4. The device of claim 3, further comprising:

a display device in communication with the processor, the display device being capable of displaying an image associated with the decompressed image data.

5. The device of claim 1, further comprising:

a compact flash memory device coupled to said port;

a compression component configured to compress the acquired image data in accordance with said particular image format; and a decompression component configured to decompress the image data that has been compressed in accordance with said particular image format, wherein the processor causes compressed image data output from the compression component to be stored on said compact flash memory device, and wherein the processor causes compressed image data stored on the compact flash memory device to be read from the compact flash memory device and routed to the decompression component, the decompression component decompressing the compressed image data routed thereto by the processor.

6. The device of claim 5, further comprising:

a display device in communication with the processor, the display device being capable of displaying an image associated with the decompressed image data.

7. The device of claim 5, wherein the compression and decompression components are comprised in a single integrated circuit chip.

8. The device of claim 1, wherein said particular image format is a JPEG image format.

9. The device of claim 8, wherein the device is designed for use by laypersons.

10. The device of claim 1, wherein said particular image format is a TIFF image format.

11. The device of claim 10, wherein the device is designed for use by laypersons.

12. The device of claim 1, wherein said particular image format is a DICOM image format.

13. A method of processing image data acquired by an ultrasound device, the method comprising:

processing image data acquired by the ultrasound device in accordance with a particular image format specification; and storing the processed image data on a compact flash memory device.

14. The method of claim 13, wherein the processing comprises:

compressing the acquired image data in accordance with the particular image format specification.

15. The method of claim 14, wherein the particular image format specification is a JPEG image format specification.

16. The method of claim 14, wherein the particular image format specification is a TIFF image format specification.

17. A method of processing ultrasound image data, the method comprising:

reading image data stored on a compact flash memory device from the compact flash memory device;

processing the image data read from the compact flash memory device in accordance with a particular image format specification; and displaying an ultrasound image corresponding to the processed image data on a display device.

18. The method of claim 17, wherein the processing comprises:

decompressing the image data read from the compact flash memory device in accordance with the particular image format specification.

19. The method of claim 17, wherein the particular image format specification is a JPEG image format specification.

20. The method of claim 17, wherein the particular image format specification is a TIFF image format specification.

21. A computer program to process image data acquired by an ultrasound device, the computer program being stored on a computer-readable medium, the program comprising:

a first code segment to process the image data in accordance with a particular image format specification;

a second code segment to store the processing image data on a compact flash memory device.

22. A computer program to process ultrasound image data in an ultrasound device, the computer program being stored on a computer-readable medium, the program comprising:

a first code segment to read image data stored on a compact flash memory device from the compact flash memory device; and a second code segment to cause an ultrasound image corresponding to the image data read from the compact flash memory device to be displayed on a display device of the ultrasound device.

* * * * *